(12) United States Patent
Gaudin et al.

(10) Patent No.: US 7,985,403 B2
(45) Date of Patent: Jul. 26, 2011

(54) 4-DODECENE DERIVATIVES AS PERFUMING INGREDIENTS

(75) Inventors: Jean-Marc Gaudin, Annemasse (FR); Wessel-Jan Kos, Beaconsfield (GB)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 12/530,779

(22) PCT Filed: Mar. 25, 2008

(86) PCT No.: PCT/IB2008/051109
§ 371 (c)(1),
(2), (4) Date: Sep. 10, 2009

(87) PCT Pub. No.: WO2008/125994
PCT Pub. Date: Oct. 23, 2008

(65) Prior Publication Data
US 2010/0008881 A1    Jan. 14, 2010

(30) Foreign Application Priority Data
Apr. 16, 2007   (WO) ............... PCT/IB2007/051354

(51) Int. Cl.
*A61K 8/40* (2006.01)
*A61Q 15/00* (2006.01)
*A61Q 13/00* (2006.01)
*A61L 9/01* (2006.01)
*C07C 255/07* (2006.01)
*C07C 251/40* (2006.01)

(52) U.S. Cl. .......... 424/65; 424/76.2; 558/462; 564/268

(58) Field of Classification Search ................. 424/65, 424/76.5; 558/462; 564/268
See application file for complete search history.

(56) References Cited

U.S. PATENT DOCUMENTS

| 3,960,923 A | 6/1976 | DeSimone ............... 260/465.9 |
| 2005/0148492 A1 | 7/2005 | Mankee et al. ............... 512/1 |

FOREIGN PATENT DOCUMENTS

| EP | 0672746 | 9/1995 |
| EP | 672746 B1 * | 5/2002 |
| JP | 57134457 | 8/1982 |
| NL | 7713925 | 6/1979 |
| NL | 7713925 A * | 6/1979 |
| WO | WO 02/059079 | 8/2002 |
| WO | WO 2005/047232 | 5/2005 |
| WO | WO 2006/060931 | 6/2006 |

OTHER PUBLICATIONS

S. Arctander, Perfume and Flavor Chemicals, 1969, Montclair, N.J. (disclosed in the IDS).*
Hoernfeldt et al., Acta Chemica Scandinavia, 1994, vol. 48(8), p. 665-9.*
International Search Report, PCT/IB2008/051109, mailed Aug. 19, 2008.
1121: Dodecyl Nitrile Compound (2 pages), (1969), based on the specification.

* cited by examiner

*Primary Examiner* — Yong Chu
(74) *Attorney, Agent, or Firm* — Winston & Strawn LLP

(57) ABSTRACT

The present invention relates to the field of perfumery. More particularly, it concerns specific oxime or nitrite derivatives of 4-dodecene, which are useful perfuming ingredients in particular to impart natural mandarin odor notes.

22 Claims, No Drawings

4-DODECENE DERIVATIVES AS PERFUMING INGREDIENTS

This application is a 371 filing of International Patent Application PCT/IB2008/051109 filed Mar. 25, 2008.

TECHNICAL FIELD

The present invention relates to the field of perfumery. More particularly, it concerns specific nitrogen-containing 4-dodecene derivatives, which are useful perfuming ingredients. The present invention concerns also the use of said compound in the perfumery industry as well as the compositions or articles containing said compound.

PRIOR ART

To the best of our knowledge, none of the invention's compounds is known.

The corresponding saturated nitrile, i.e. dodecyl nitrile, is known in perfumery as being a useful ingredient (see S. Arctander, Perfume and Flavor Chemicals, 1969, Montclair, N.J., USA, compound N°1121). However, said structural analogue possesses organoleptic properties totally different from the ones of the present invention's nitrile. Furthermore, nowhere in the prior art citing this structural analogue it is suggested or anticipated that the present compounds could be used as perfuming ingredients, and in particular to confer their particular fragrance.

DESCRIPTION OF THE INVENTION

We have now surprisingly discovered that a compound of formula

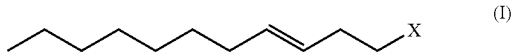

(I)

wherein X represents a CN or a HC=N—OH group, and the carbon carbon-double bond has a configuration E or Z, or a mixture thereof,
can be used as perfuming ingredient, for instance to impart odour notes of the mandarine type.

As mentioned above, a compound (I) can be in the form of its E isomer or Z isomer, or even in the form of a mixture thereof. According to a particular embodiment of the invention, particularly appreciated compounds of formula (I) are those which are in the form of a mixture of isomers (4Z) and (4E) in a ratio ranging from 80/20 to 99.5/0.5. According to a further embodiment of the compound (I), the carbon carbon-double bond has a configuration Z.

As particular examples of invention's compounds, one may cite (4Z)-4-dodecenenitrile which possesses a powerful and exceptionally natural mandarin odour, typical of a mature mandarin and its juice.

The odour of said nitrile is of high interest to the perfumers since only very few compounds are known to possess a mandarin odour, i.e. (4Z)-4-dodecenal and Sinensal (2,6,10-trimethyl-2(E),6(E),9(E),11-dodecatetraenal).

The odour of (4Z)-4-dodecenenitrile is reminiscent of the one of Sinensal (which possesses a chemical structure very different and is of very difficult preparation).

However, when the odour of the invention's compounds is compared with the one of (4Z)-4-dodecenal, important olfactive differences pop up. For instance (4Z)-4-dodecenenitrile possesses a much more natural, warm balanced odour typical of the mature fruit, while the (4Z)-4-dodecenal possesses a more acidic, aggressive character typical of the green fruit wherein the typical "wet dog" aspect of the mature fruit is much less pronounced than in the odour of the nitrile. In other words, the invention's nitrile possesses an odour that completes the perfumer's palette for the mandarin notes.

When the odour of (4Z)-4-dodecenenitrile is compared with the one of its saturated nitrile analogue dodecyl nitrile, the differences are even more striking. Indeed, (4Z)-4-dodecenenitrile does not possess herbal, fatty or woody notes which are so typical of dodecyl nitrile. Furthermore, the latter compound is only vaguely reminiscent of orange peel and not at all mandarin like.

As another particular example of invention's compounds, one may cite (4Z)-4-dodecenenal oxime which imparts a mandarin note with a slightly green aspect. The odour of this oxime is less pronounced than the one of the above-cited nitrile.

As mentioned above, the invention concerns the use of a compound of formula (I) as perfuming ingredient. In other words it concerns a method to confer, enhance, improve or modify the odour properties of a perfuming composition or of a perfumed article, which method comprises adding to said composition or article an effective amount of at least a compound of formula (I). According to a particular embodiment of the invention, said method or use is particularly appreciated to impart odour notes of the mandarin type.

By "use of a compound of formula (I)" it has to be understood here also the use of any composition containing compound (I) and which can be advantageously employed in the perfumery industry as active ingredients.

Said composition, which in fact can be advantageously employed as perfuming ingredient, is also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

As solid carrier one may cite, as non-limiting examples, absorbing gums or polymers, or yet encapsulating materials. Examples of such materials may comprise wall-forming and plasticizing materials, such as mono-, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs-und Geheermittel in Lebensmittel, Band 2 der Schriftenreihe Lebensmittelchemie, Lebensmittelqualität, Behr's VerlagGmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

By "perfumery base" we mean here a composition comprising at least one perfuming co-ingredient.

Said perfuming co-ingredient is not of the formula (I). Moreover, by "perfuming co-ingredient" it is meant here a compound, which is used in perfuming preparation or composition to impart a hedonic effect. In other words such a co-ingredient, to be considered as being a perfuming one, must be recognized by a person skilled in the art as being able to impart or modify in a positive or pleasant way the odour of a composition, and not just as having an odour.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitriles, terpene hydrocarbons, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

For the compositions which comprise both a perfumery carrier and a perfumery base, suitable perfumery carrier, other than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

According to a particular embodiment of the invention, said composition may comprise (4Z)-4-dodecenenitrile and dodecyl nitrile in a w/w ratio ranging from about 80/20 to 95/5.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odour tonality of various compounds of the invention, creating thus new tools for their work.

Preferably, any mixture resulting directly from a chemical synthesis, e.g. without an adequate purification, in which the compound of the invention would be involved as a starting, intermediate or end-product could not be considered as a perfuming composition according to the invention.

Furthermore, the invention's compound can also be advantageously used in all the fields of modern perfumery to positively impart or modify the odour of a consumer product into which said compound (I) is added. Consequently, a perfumed article comprising:

i) as perfuming ingredient, at least one compound of formula (I), as defined above, or an invention's perfuming composition; and ii) a consumer product base;

is also an object of the present invention.

For the sake of clarity, it has to be mentioned that, by "consumer product base", we mean here a consumer product, which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer product bases include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the invention's compound, so that it may be necessary to protect the latter from premature decomposition, for example by encapsulation.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.001% to 1.0% by weight, or even more, of the compounds of the invention based on the weight of the composition into which they are incorporated. Concentrations lower than these, such as in the order of 0.01% to 0.5% by weight, can be used when these compounds are incorporated into perfumed articles, percentage being relative to the weight of the article.

The invention's compounds can be prepared by transforming the 4-dodecenal into the corresponding oxime, by any means commonly known by a person skilled in the art, and then, optionally, by transforming the oxime into the desired nitrile, by any means commonly known by a person skilled in the art.

EXAMPLES

The invention will now be described in further detail by way of the following examples, wherein the abbreviations have the usual meaning in the art, the temperatures are indicated in degrees centigrade (° C.); the NMR spectral data were recorded in CDCl$_3$ (if not stated otherwise) with a 360 or 400 MHz machine for $^1$H and $^{13}$C, the chemical displacements δ are indicated in ppm with respect to TMS as standard, the coupling constants J are expressed in Hz.

Example 1

Synthesis of Compounds of (4Z)-4-dodecenenal oxime

In a 250 ml three-necked flask containing 20 g of (Z)-4-dodecenal in 50 ml of cyclohexane were added 8.4 ml of NH$_2$OH (50% aqueous solution) over 30 minutes. The reaction was left overnight. The organic layer was decanted, washed with water and the solvent removed in vacuum to yield the oxime as a mixture 55/45 of 1-E and 1-Z.

MS (major isomer): m/z (%): 197 [M+] (1), 180 (38), 178 (6), 152 (9), 138 (8), 136 (7), 124 (8), 122 (10), 112 (25), 96 (70), 95 (68), 82 (100), 67 (49), 55 (68), 43 (80), 41 (97).

MS (minor isomer): m/z (%): 180 (6), 152 (9), 138 (6), 136 (7), 124 (10), 122 (12), 110 (15), 108 (21), 96 (80), 95 (74), 82 (96), 67 (53), 55 (70), 43 (88), 41 (100).

Synthesis of Compounds of (4Z)-4-dodecenenitrile

The oxime obtained above was charged into a flask with 20 ml of acetic anhydride and 0.2 g of potassium acetate. The reaction was heated at 100° C. during 1 hour, then cooled at room temperature, hydrolyzed and extracted with Et$_2$O. The organic layer was washed three times with water, dried with MgSO$_4$ and the solvent concentrated. Purification by flash chromatography (cyclohexane/ethylacetate=97/3) gave 14.2 g of the pure nitrile (72% yield).

$^1$H-NMR: 0.88 (t, J=7, 3H), 1.24-1.40 (m, 10H), 2.05 (q, J=7, 2H), 2.35-2.43 (m, 4H), 5.37 (m, 1H), 5.56 (m, 1H).

$^{13}$C-NMR: 14.1 (q), 17.6 (t), 22.7 (t), 23.3 (t), 27.3 (t), 29.2 (t), 29.3 (t), 29.5 (t), 31.9 (t), 119.4 (s), 125.0 (d), 133.7 (d).

Example 2

Preparation of a Perfuming Composition

A perfuming composition of the mandarin type was prepared by admixing the following ingredients:

| Ingredient | Parts by weight |
| --- | --- |
| Benzyl acetate | 60 |
| Aldehyde C 10 | 15 |
| Aldehyde C 12 | 30 |
| Aldehyde C 8 | 5 |
| Aldehyde C 9 | 5 |
| Aldehyde MNA | 10 |
| 9-Undecenal | 10 |
| Citral | 10 |
| 3,7-Dimethyl-6-octenenitrile | 20 |
| Hedione ®[1] | 100 |
| Allyl heptanoate | 5 |
| Linalool | 200 |
| Methyl methylanthranilate | 30 |
| Sclareolate ®[2] | 200 |
| Pinenes | 20 |
| Terpenes ex orange | 200 |
| Terpineol | 80 |
| | 1000 |

[1] Methyl dihydrojasmonate; origin: Firmenich SA, Geneva, Switzerland

[2] Propyl (S)-2-(1,1-dimethylpropoxy)propanoate; origin: Firmenich SA, Geneva, Switzerland The addition of 10 parts by weight of a 10% solution of (4Z)-4-dodecenenitrile in dipropyleneglycol to the above-described perfuming composition imparted to the latter an excellent natural mandarin character strongly reminding of the odour of the best Sicilian mandarin.

When to the above-mentioned composition was added the same amount of (4Z)-4-dodecenal, the new fragrance was less natural, much more acidic and green, i.e. it had a mandarin character quite different from the one containing the invention's nitrile.

When to the above-mentioned perfuming base was added the same amount of dodecyl nitrile, the composition's scent lost the mandarin character and became less elegant, more functional and fatty.

Example 3

Preparation of a Perfuming Composition

A perfuming composition, for woman, of the oriental type was prepared by admixing the following ingredients:

| Ingredient | Parts by weight |
| --- | --- |
| Benzyl acetate | 20 |
| 50%* Cinnamic alcohol | 10 |
| Hexyl cinnamic aldehyde | 10 |
| 50%* Benjoin essential oil | 30 |
| Bergamot essential oil | 50 |
| 8-Methoxy-2,6,6,8-tetramethyl-tricyclo[5.3.1.0(1,5)]undecane | 10 |
| Lemon essential oil | 15 |
| 10%* Civette | 15 |
| 4-Cyclohexyl-2-methyl-2-butanol | 20 |
| Coumarine | 15 |
| 10%* Decal | 10 |
| 10%* Ethylvanilline | 20 |
| Eugenol | 10 |
| Hedione ®[1] HC | 30 |
| Hydroxycitronellal | 35 |
| Iso E Super ®[2] | 50 |
| 10%* Jasmin essential oil | 25 |
| Linalol | 40 |
| Mandarin essential oil | 25 |
| Muscenone[3] | 50 |
| 10%* (E)-4-(2,2,C-3,T-6-Tetramethyl-R-1-cyclohexyl)-3-buten-2-one | 10 |
| 10%* Nirvanol ®[4] | 25 |
| Patchouli essential oil | 40 |
| 10%* Perou baume | 30 |
| Benzyl salicylate | 260 |
| (Z)-3-hexen-1-yl salicylate | 25 |
| Sclareolate ®[5] | 15 |
| Vanilline | 10 |

-continued

| Ingredient | Parts by weight |
|---|---|
| Vetyver | 10 |
| Wardia ®[6] | 50 |
| 10%* Ylang | 25 |
| | 990 |

*in dipropyleneglycol
[1] Methyl dihydrojasmonate; origin: Firmenich SA, Geneva, Switzerland
[2] 1-(Octahydro-2,3,8,8-tetramethyl-2-naphtalenyl)-1-ethanone; origin: International Flavors & Fragrances, USA
[3] 3-Methyl-(4/5)-cyclopentadecenone; origin: Firmenich SA, Geneva, Switzerland
[4] 3,3-Dimethyl-5-(2,2,3-trimethyl-3-cyclopenten-1-yl)-4-penten-2-ol; origin: Firmenich SA, Geneva, Switzerland
[5] Propyl (S)-2-(1,1-dimethylpropoxy)propanoate; origin: Firmenich SA, Geneva, Switzerland
[6] Compounded perfumery base (floral type); origin: Firmenich SA, Geneva, Switzerland The addition of 10 parts by weight of a 1% solution of (4Z)-4-dodecenenitrile in dipropyleneglycol to the above-described perfuming composition reinforced considerably the warm natural juicy citrus-mandarin character of this oriental perfume.

When to the above-mentioned composition was added the same amount of (4Z)-4-dodecenal or of dodecyl nitrile, the differences observed were similar to the ones mentioned above.

The invention claimed is:

1. A compound of formula

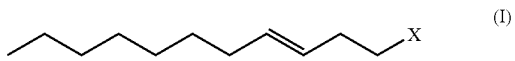 (I)

wherein X represents a HC=N—OH group, and the carbon carbon-double bond has a configuration E or Z, or a mixture thereof.

2. A mixture of compounds of formula (I)

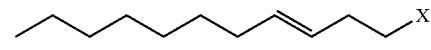 (I)

wherein X represents a CN or a HC=N—OH group, and the carbon carbon-double bond has a configuration E or Z, comprising in the form of a mixture of isomers (4Z) and (4E), in a ratio ranging from 80/20 to 99.5/0.5.

3. The mixture according to claim 2, which includes (4Z)-4-dodecenenitrile or (4Z)-4-dodecenenal oxime.

4. A perfuming composition comprising
i) at least one compound of formula

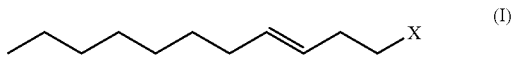 (I)

wherein X represents a HC=N—OH group, and the carbon carbon-double bond has a configuration E or Z, or a mixture thereof;
ii) at least one ingredient selected from the group consisting of a perfumery carrier and a perfumery base; and
iii) optionally at least one perfumery adjuvant.

5. A perfumed article comprising:
i) as perfuming ingredient, at least one compound of formula

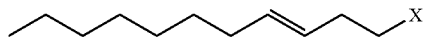 (I)

wherein X represents a HC=N—OH group, and the carbon carbon-double bond has a configuration E or Z, or a mixture thereof; and
ii) a consumer product base;

6. A perfumed article according to claim 5, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

7. A method to confer, enhance, improve or modify the odor properties of a perfuming composition or of a perfumed article, which method comprises adding to said composition or article an effective amount of at least a compound of formula

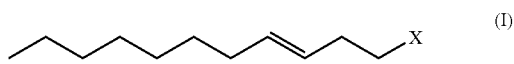 (I)

wherein X represents a CN or a HC=N—OH group, and the carbon carbon-double bond has a configuration E or Z, or a mixture thereof in an amount effective to impart a mandarin odor note to the composition or article.

8. A method according to claim 7, wherein the compound is added in an amount of between 0.001 and 1% by weight of the composition or article.

9. The method of claim 8, wherein the compound of formula I comprises (4Z)-4-dodecenenitrile or (4Z)-4-dodecenenal oxime.

10. The method of claim 7, wherein the compound of formula (I) comprises a mixture of (4Z)-4-dodecenenitrile and dodecyl nitrile in a w/w ratio ranging from about 80/20 to 95/5.

11. The method of claim 7, wherein the compound of formula (I) comprises a mixture of compounds of formula (I)

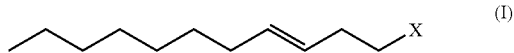 (I)

wherein X represents a CN or a HC=N-OH group, and the carbon carbon-double bond has a configuration E or Z, comprising in the form of a mixture of isomers (4Z) and (4E), in a ratio ranging from 80/20 to 99.5/0.5.

12. A method to confer, enhance, improve or modify the odor properties of a perfuming composition or of a perfumed article, which method comprises adding to said composition or article an effective amount of at least a compound of formula

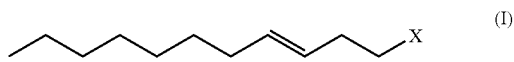 (I)

wherein X represents a HC=N-OH group, and the carbon carbon-double bond has a configuration E or Z, or a mixture thereof.

13. A method according to claim 7, wherein the compound is added in an amount of between 0.001 and 1% by weight of the composition or article.

14. A perfuming composition comprising
i) a mixture of compounds of formula

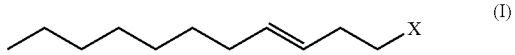 (I)

wherein X represents a CN or a HC=N-OH group, and the carbon carbon-double bond has a configuration E or Z, in the form of a mixture of isomers (4Z) and (4E) in a ratio ranging from 80/20 to 99.5/0.5;
ii) at least one ingredient selected from the group consisting of a perfumery carrier and a perfumery base; and
iii) optionally at least one perfumery adjuvant.

15. The perfuming composition of claim 4 wherein the compound is (4Z)-4-dodecenal oxime.

16. A perfuming composition comprising:
i) a mixture of (4Z)-4-dodecenenitrile and dodecyl nitrile in a w/w ratio ranging from about 80/20 to 95/5;
ii) at least one ingredient selected from the group consisting of a perfumery carrier and a perfumery base; and
iii) optionally at least one perfumery adjuvant.

17. A perfumed article comprising: i) as perfuming ingredient, a mixture of compounds of formula

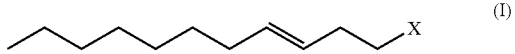 (I)

wherein X represents a CN or a HC=N-OH group, and the carbon carbon-double bond has a configuration E or Z, in the form of a mixture of isomers (4Z) and (4E) in a ratio ranging from 80/20 to 99.5/0.5; and
ii) a consumer product base.

18. The perfumed article of claim 17, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

19. The perfumed article of claim 5, wherein the compound is (4Z)-4-dodecenenal oxime.

20. The perfumed article of claim 19, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

21. A perfumed article comprising:
i) as perfuming ingredient, a mixture of (4Z)-4-dodecenenitrile and dodecyl nitrile in a w/w ratio ranging from about 80/20 to 95/5; and
ii) a consumer product base.

22. The perfumed article of claim 21, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

* * * * *

UNITED STATES PATENT AND TRADEMARK OFFICE
CERTIFICATE OF CORRECTION

| | | |
|---|---|---|
| PATENT NO. | : 7,985,403 B2 | Page 1 of 1 |
| APPLICATION NO. | : 12/530779 | |
| DATED | : July 26, 2011 | |
| INVENTOR(S) | : Gaudin et al. | |

It is certified that error appears in the above-identified patent and that said Letters Patent is hereby corrected as shown below:

Title Page:
Item (57) Abstract, line 2, change "nitrite" to -- nitrile --.

Column 8:
Line 9, after "ii) a consumer product", change "base;" to -- base. --.
Line 36, after "claim" change "8," to -- 7, --.

Column 9:
Line 27, after "comprising:", start a new subparagraph with "i) as perfuming ingredient".

Signed and Sealed this
Thirteenth Day of September, 2011

David J. Kappos
*Director of the United States Patent and Trademark Office*